United States Patent
Kumar et al.

(10) Patent No.: US 6,511,822 B1
(45) Date of Patent: Jan. 28, 2003

(54) IMMOBILIZED MICROBIAL CONSORTIUM USEFUL FOR RAPID AND RELIABLE BOD ESTIMATION

(75) Inventors: Rita Kumar, Delhi (IN); Alka Sharma, Delhi (IN); Shikha Rastogi, Delhi (IN); Santosh Dayaram Makhijani, Delhi (IN); A. Manoharan, Delhi (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/982,139

(22) Filed: Oct. 18, 2001

Related U.S. Application Data

(62) Division of application No. 09/537,440, filed on Mar. 27, 2000.
(51) Int. Cl.⁷ .................................................. C12P 39/00
(52) U.S. Cl. .......................................................... 435/42
(58) Field of Search .......................................... 435/42

(56) References Cited

FOREIGN PATENT DOCUMENTS

| | | |
|---|---|---|
| DE | 4301087 | 7/1994 |
| EP | 0543407 | 5/1993 |
| JP | 4337453 | 11/1992 |

OTHER PUBLICATIONS

WP1 English Abstract of DE 4301087 Dated Jul. 21, 1994.
WP1 English Abstract of JP 4337453 Dated Nov. 25, 1992.

*Primary Examiner*—Herbert J. Lilling
(74) *Attorney, Agent, or Firm*—Ladas & Parry

(57) ABSTRACT

An immobilized microbial consortium is formulated which comprises of a synergistic mixture of isolated bacteria namely, *Aeromonas hydrophila, Pseudomonas aeruginosa, Yersinia enterocolitica, Serratia liquefaciens, Pseudomonas fluoresces, Enterobacter cloaca, Klebsiella oxytoca, Citrobacter amalonaticus* and *Enterobacter sakazaki*. The formulated microbial consortium is immobilized on charged nylon membrane. The said immobilized microbial consortium is attached to dissolved oxygen probe for the preparation of electrode assembly. The prepared electrode assembly is used for rapid and reliable BOD estimation. The prepared electrode assembly is used for monitoring of BOD load of synthetic samples such as Glucose-Glutamic acid (GGA) used as a reference standard in BOD analysis and industrial effluents; covering a range from low to high biodegradable organic matter.

14 Claims, No Drawings

IMMOBILIZED MICROBIAL CONSORTIUM USEFUL FOR RAPID AND RELIABLE BOD ESTIMATION

This applications is a divisional of 09/537,440 filed Mar. 27, 2000.

FIELD OF THE INVENTION

The present invention relates to an immobilized microbial consortium and a process for the preparation of the said immobilized microbial consortium, useful for rapid and reliable BOD estimation.

DESCRIPTION OF THE PRIOR ART

Rapid analytical devices have attracted tremendous interest and attention in science and technology for their wide range of possible application as an alternative to conventional analytical techniques. Analytical devices are sensitive to biological parameters and consist of a biological sensing element such as microbes, enzymes, etc., in close contact with a physico-chemical transducer such as an electrode, which converts biological signal to a quantitative response. These devices have several unique features such as compact size, simple to use, one step reagent-less analysis, low cost and quick real time results.

Rapid analytical devices, termed as biosensors, have the potential for a major impact in the human health care, environmental monitoring, food analysis and industrial process control. Among these, microbial biosensors (the devices using microbes as biological component), have great potential in environmental monitoring. Recent trends in biotechnology suggest that monitoring and control of pollutant by means of microbial biosensors may be of crucial importance. Such microbial sensors, constructed by entrapping the required micro-organisms in suitable polymeric matrices and attached to a transducer, function on the basis of assimilatory capacity of the micro-organisms. In addition, microbial biosensors are more stable and inexpensive for the determination of compounds of interest as compared to enzyme-based biosensors; where enzymes employed in enzyme-based biosensors require costly extraction and purification prior to use as biocatalysts. Further, micro-organisms employed in microbial biosensors show a high degree of stability as compared to enzymes.

The vast majority of micro-organisms are relatively easy to maintain in pure cultures, grow and harvest at low cost. Moreover, the use of microbes in biosensor field have opened up new possibilities and advantages such as ease of handling, preparation and low cost of the device. Such devices will help in monitoring the compounds of environmental interest such as Biochemical Oxygen Demand (BOD), heavy metals, pesticides, phenols, etc.

Among the environmental parameters, the potential demand for rapid BOD monitoring device is higher, since, BOD is a parameter which is measured most frequently by many industries for measuring the level of pollution of waste-waters. BOD provides information about the amount of biodegradable substances in waste-waters.

Conventional BOD test takes 3–5 days and as a consequence, is unsuitable for use in direct process control. A more rapid estimation of BOD is possible by developing a BOD biosensor. Such BOD biosensors are able to reduce the time of BOD test upto a great extent.

A number of microbial BOD sensors have been developed nationally and internationally (Rajasekar et al, 1992 and Karube, 1977). A number of pure cultures, eg., *Trichosporon cutaneum, Hansenula anamola, Bacillus cereus, Bacillus subtilis, Klebsiella oxytoca*, Pseudomonas sp., etc., individually, have been used by many workers for the construction of BOD biosensor (Preinenger et al, 1994; Hyun et al, 1993, Li and Chu 1991; Riedel et al, 1989 and Sun and Kiu, 1992). Karube et al, (1992) developed a BOD biosensor by utilizing thermophilic bacteria isolated from Japanese hot spring. On the other hand, most of the workers have immobilized activated sludge (Vanrolleghem et al 1990; Kong et al 1993; Vanrolleghem et al, 1984), or a mixture of two or three bacterial species (Iki, 1992 and Galindo et al 1992) on various membranes for the construction of BOD biosensor. The most commonly used membranes were polyvinyl alcohol, porous hydrophilic membranes, etc. Riedel et al, (1988), have used polyvinyl alcohol for the immobilization of *Bacillus subtilis* or *Trichosporon cutaneum* which are used for the development of BOD biosensor. Vinegar (1993) immobilized *Klebsiella oxytoca* on porous hydrophilic membranes such as nitrocellulose, acetyl cellulose, polyvinylidene flouride or polyether sulfone, 50–2000 micrometer thick. Cellulose acetate membrane was used for the immobilization of *Lipomyces kononankoae* and *Asperillus niger* (Hartmeier et al, 1993).

The drawback of such developed BOD biosensors which are constructed by using either single, pure culture or activated sludge is that they do not give reproducible results, as single microbe is not able to assimilate/degrade all the organic compounds and therefore may not respond for the total organic matter present in the test sample (eg., carbohydrates, proteins, fats, grease, etc.) Moreover, in the activated sludge either non-specific predominating, microorganisms are present thereof or microorganisms with antagonistic effects are present which may produce erratic results. On the other hand, randomly selected mixtures of two or three micro-organisms also do not give reproducible, comparable BOD results. The reproducibility of the BOD biosensor can be obtained by formulating a defined microbial composition.

To avoid the discrepancies in BOD results as well as to get instant BOD values using rapid analytical devices, in the present invention, a defined microbial composition is formulated by conducting a systematic study, i.e., pre-testing of selected micro-organisms for use as a seeding material in BOD analysis of a wide variety of industrial effluents. The formulated microbial consortium is capable of assimilating most of the organic matter present in different industrial effluents. The formulated microbial consortium has been immobilized on suitable membrane i.e., charged nylon membrane useful for BOD estimation. Suitability of the charged nylon membrane lies in the specific binding between the negatively charged bacterial cell and positively charged nylon membrane. So, the advantages of the used membrane over other membranes are the dual binding i.e., adsorption as well as entrapment thus resulting in a more stable immobilized membrane. Such specific microbial consortium based BOD analytical devices, may find great application in, on-line monitoring of the degree of pollutional strength, in a wide variety of industrial waste-waters within a very short time (from 3–5; days to within an hour), which is very essential from pollution point of view.

For solving the aforementioned problems, the applicants have realized that there exists a need to provide a process for the preparation of a defined synergistic microbial consortium immobilized on a suitable support i.e., charged nylon membrane, useful for BOD estimation. The said microbial consortium is capable of assimilating most of the organic matter present in different industrial effluents.

OBJECTS OF THE INVENTION

The main object of the present invention is to provide a microbial consortium and a process for the preparation of the microbial consortium immobilized on a suitable support useful for BOD estimation.

The formulated microbial consortium comprises of cultures of the following bacteria viz., *Aeromonas hydrophila, Pseudomonas aeruginosa, Yersinia enterocolitica, Serratia liquefaciens, Pseudomonas fluorescens, Enterobacter cloaca, Klebsiella oxytoca, Citrobacter amalonaticus* and *Enterobacter sakazaki*. The individual bacteria of microbial consortium are pre-tested by using them as a seeding material in BOD analysis of a wide variety of industrial effluents. The micro-organisms have been selected for the formulation of microbial consortium on the basis of pretesting. The formulated microbial consortium is obtained by inoculating a suspension of these bacteria individually. Incubating at 37° C., mixing all bacterial cultures in equal proportions based on optical density and centrifuging. The resultant pellet is immobilized on suitable support, i.e., charged nylon membrane by entrapment and adsorption on the charged surface of the membrane. The said, charged immobilized microbial membrane has high viability, long stability and greater shelf-life as compared to the microbial consortium immobilized on conventional supports such as polyvinyl alcohol+nylon cloth.

Accordingly, another object of the present invention, is to provide a process for the production of immobilized formulated microbial consortium useful for monitoring the BOD load of a wide range of industrial effluents with low, moderate and high BOD load.

SUMMARY OF THE INVENTION

The present invention provides an immobilized microbial consortium and a process for the preparation of the said immobilized microbial consortium, useful for rapid and reliable BOD estimation of a wide range of industrial effluents with low, moderate and high BOD load.

DETAILED DESCRIPTION OF THE INVENTION

The microbial consortium provided according to the present invention contains bacteria consisting of:

| Sl. No. | Cultures | CBTCC Accession No. | Patent Deposit Designation | Prior art strains having characteristics to that of CBTCC No. |
|---|---|---|---|---|
| 1. | Aeromonas hydrophila deposited with ATCC on Aug. 27, 2001 | CBTCC/MICRO/10 | PTA-3751 | ATCC 7966 |
| 2. | Pseudomonas aeruginosa deposited with ATCC on Aug. 27, 2001 | CBTCC/MICRO/3 | PTA-3748 | ATCC 49622 |
| 3. | Yersinia enterocolitica deposited with ATCC on Aug. 27, 2001 | CBTCC/MICRO/4 | PTA-3752 | ATCC 27739 |
| 4. | Serratia liquefaciens deposited with DSMZ on May 28, 2002 | CBTCC/MICRO/7 | DSM 15081 | ATCC 25641 |
| 5. | Pseudomonas fluorescens deposited with ATCC on Aug. 27, 2001 | CBTCC/MICRO/11 | PTA-3749 | ATCC 13525 |
| 6. | Enterobacter cloaca deposited with ATCC on Nov. 28, 2001 | CBTCC/MICRO/1 | PTA-3882 | ATCC 29893 |
| 7. | Klebsiella oxytoca deposited with DSMZ on May 28, 2002 | CBTCC/MICRO/5 | DSM 15080 | ATCC 15764 |
| 8. | Citrobacter amalonaticus deposited with DSMZ on May 28, 2002 | CBTCC/MICRO/2 | DSM 15079 | ATCC 25406 |
| 9. | Enterobacter sakazaki deposited with DSMZ on May 28, 2002 | CBTCC/MICRO/6 | DSM 15063 | ATCC 12868 |

The above micro-organisms are deposited with the American Type Culture Collection, Manasses, Va., USA and Deutsche Sammlung Von Mikroorganimen Und Zellkulturen GmbH, Mascheroder Weg 1b, D-38124 Braunschweig, Germany on the dates and with designations as stated above.

| | CBTCC ACCESSION NO. | PATENT DEPOSIT DESIGNATION |
|---|---|---|
| Characteristic features of *Aeromonas hydrophila* Gram negative rods Motile by a single polar flagellum Metabolism of glucose is both respiratory and fermentative Oxidase positive Catalase positive Ferments salicin, sucrose and mannitol | (CBTCC/MICRO/10) | PTA-3751 |
| Characteristic features of *Pseudomonas aeruginosa* Gram negative, aerobic rods shaped bacteria Have polar flagella Metabolism is respiratory, never fermentative Oxidase positive Catalase positive Denitrification positive | (CBTCC/MICRO/3) | PTA-3748 |
| Characteristic features of *Yersinia enterocolitica* Gram negative rods | (CBTCC/MICRO/4) | PTA-3752 |

-continued

| | CBTCC ACCESSION NO. | PATENT DEPOSIT DESIGNATION |
|---|---|---|
| Facultative anaerobic, having both respiratory and fermentative type of metabolism Oxidase negative Motile Produces acid from sucrose, cellobiose, sorbose and sorbitol Characteristic features of *Serratia liquefaciens* | (CBTCC/MICRO/7) | DSM 15081 |
| Gram negative, facultative anaerobic rods Motile and have peritrichous flagella Produces acid from L-arabinose, D-xylose and D-sorbitol Tween 80 Hydrolysis positive Lysine carboxylase and ornithine carboxylase positive Characteristic features of *Pseudomonas fluorescens* | (CBTCC/MICRO/11) | PTA-3749 |
| Gram negative, aerobic rod shaped bacteria Have polar flagella Metabolism is respiratory, never fermentative Catalase positive Produces pyoverdin Gelatin liquefaction positive Characteristic features of *Enterobacter cloaca* | (CBTCC/MICRO/1) | PTA-3882 |
| Gram negative straight rods Motile by peritrichous flagella Facultative anaerobe Ferments glucose with production of acid and gas KCN and gelatinase positive Nitrate reductase positive Characteristic features of *Klebsiella oxytoca* | (CBTCC/MICRO/5) | DSM 15080 |
| Gram negative, facultative anaerobic rods Non-motile Oxidase negative Positive for Voges Proskauer test Utilizes citrate, m-hydroxybenzoate and degrades pectin Ferments L-arabinose, myoinositol, lactose, sucrose and raffinose Characteristic features of *Citrobacter amalonaticus* | (CBTCC/MICRO/2) | DSM 15079 |
| Gram negative, facultative anaerobic rods Facultative anaerobic Motile Indole production positive Utilizes malonate Esculin hydrolysis positive Characteristic features of *Enterobacter sakazaki* | (CBTCC/MICRO/6) | DSM 15063 |
| Gram-negative, facultative anaerobic rods Motile by peritrichous flagella Produces a non-diffusible yellow pigment at 25° C. Utilizes citrate Gelatinase and β-xylosidase positive Produces acid from sucrose, raffinose and α-methylglucoside | | |

The microbial consortium may contain the bacteria, in a preferred embodiment of the invention, in uniform amounts.

The microbial consortium of the present invention is useful for BOD estimation.

The bacterial cultures of the above microbial consortium are isolated from sewage. Sewage samples are collected from Okhla Coronation Plant near Okhla, New Delhi. Sewage is homogenized for 2 minutes and suspended in gram-negative culture broth. Incubation is carried out for 24 hours. Cultures are plated on Mac Conkey's agar. Colonies are mixed on a vortex mixer and all the cultures are isolated in pure form after several sub-cultures.

The immobilization technique of formulated microbial consortium of the present invention is carried out by inoculating the individual strains of the above mentioned bacteria separately in nutrient broth containing (per litre), 5.0 g peptic digest of animal tissue, 5.0 g of sodium chloride, 1.5 g of beef extract, 1.5 g yeast extract and 0.2 ml tween-80. All the cultures are incubated preferably at 37° C. for approximately 16–24 hours in an incubator shaker. For gentle shaking, the incubator shaker is maintained at an appropriate rpm, preferably at 75 rpm. After sufficient growth is obtained, the bacterial cells from these individual cultures are taken in equal proportions based on optical density and then mixed for formulating microbial consortium. The resultant bacterial suspension is centrifuged at an appropriate rpm, preferably at 10,000 rpm for a period of 20 minutes. The resultant pellet is washed by dissolving in minimum quantity of phosphate buffer, 0.05 M, pH 6.8 and recentrifuged at an appropriate rpm, preferably at 10,000 rpm for a period of approximately 20 minutes. During centrifugation, the temperature is maintained preferably at 4° C. The pellet thus obtained is immobilized on various membranes/supports such as charged nylon membrane and polyvinyl alcohol+nylon cloth.

For the immobilization of formulated microbial consortium on charged nylon membrane, the pellet of formulated microbial consortium is dissolved in 2 ml of phosphate buffer, 0.05M. pH 6.8 and filtered under vacuum. A number of immobilized microbial membranes are prepared under varying conditions of cell density and phase of cell growth. The immobilized microbial membranes thus obtained are left at room temperature for 4–6 hours to dry and stored at an appropriate temperature, preferably at 4° C.

For immobilization of microbial consortium on polyvinyl alcohol (high molecular weight, i.e., 70,000 to 1,00,000 hot water soluble)+nylon cloth, a strip of nylon net (approx. 4×4 inch$^2$) is tightly bound to a glass plate with the help of an adhesive. The pellet of formulated microbial consortium is dissolved in 2.0 ml phosphate buffer, 0.05M, pH 6.8 and mixed with 2% polyvinyl alcohol (PVA). The mixture of PVA and culture is poured onto a tightly bound nylon net. The mixture is spread with the help of glass rod thoroughly. A PVA+nylon cloth membrane without microorganisms is also prepared simultaneously, for control. The prepared membranes are left at room temperature for 4–6 hours to dry and then stored at an appropriate temperature, preferably at 4° C.

The immobilized microbial membranes thus obtained, are characterized with respect to cell density and phases of cell growth. For this, the individual microorganisms are grown for different time periods and a range of cell concentration is used for the immobilization on charged nylon membrane. The viability and stability of the immobilized microbial consortium is checked by storing at different pH and different temperatures. For checking the viability of immobilized microbial membranes, the membrane is placed on an agar plate in an inverted position and incubated at 37° C. overnight. The colonies were observed for growth on agar plates. For the stability study, the prepared immobilized microbial membranes are stored at different temperatures i.e., 4° C., 15° C., 25° C. & 37° C. and different pH ranging from 6.4–7.2. The response of immobilized microbial membranes is observed at regular time intervals.

To enhance the sensitivity of the response, an amperometric system is designed using dissolved oxygen (DO) probe and a highly sensitive multimeter. An external source of −0.65 volts is applied to the system to get the actual reduction of oxygen at cathode. A suitable polarization voltage i.e., −0.65 volts between the anode and cathode selectively reduces oxygen at the cathode (Karube and Chang, 1991).

For the preparation of electrode assembly, the immobilized microbial membranes are sandwiched between an oxygen permeated teflon membrane and a porous membrane, i.e., cellulose acetate membrane. The immobilized microbial membrane is fixed directly onto the platinum cathode of an commercially available $O_2$ probe.

The response characteristics of prepared immobilized microbial membranes is observed with synthetic sample i.e., glucose-glutamic acid (GGA), a reference standard used in BOD analysis. For this, the electrode assembly is dipped into a stirred $PO_4^{-3}$ buffer solution. After a stable current was obtained, known strength of GGA was injected into the reaction assembly. Consumption of oxygen by the microbial cells immobilized on membrane caused a decrease in dissolved oxygen around the membrane. As a result, the values of dissolved oxygen decreased markedly with time until a steady state is reached. The steady state indicated that the consumption of oxygen by the immobilized microbial cells and the diffusion of oxygen from the solution to the membrane are in equilibrium. This value is recorded. Consumption of oxygen by the immobilized microorganisms is observed with multimeter in terms of current (nA). The change in current is linearly related to GGA standard over the range of 30 to 300 mg/l.

| Sl. No. | Cultures | CBTCC Accession No. | Patent Deposit Designation | Prior art strains having characteristics to that of CBTCC No. |
|---|---|---|---|---|
| 1. | Aeromonas hydrophila deposited with ATCC on Aug. 27, 2001 | CBTCC/ MICRO/10 | PTA-3751 | ATCC 7966 |
| 2. | Pseudomonas aeruginosa deposited with ATCC on Aug. 27, 2001 | CBTCC/ MICRO/3 | PTA-3748 | ATCC 49622 |
| 3. | Yersinia enterocolitica deposited with ATCC on Aug. 27, 2001 | CBTCC/ MICRO/4 | PTA-3752 | ATCC 27739 |
| 4. | Serratia liquefaciens deposited with DSMZ on May 28, 2002 | CBTCC/ MICRO/7 | DSM 15081 | ATCC 25641 |
| 5. | Pseudomonas fluorescens deposited with ATCC on Aug. 27, 2001 | CBTCC/ MICRO/11 | PTA-3749 | ATCC 13525 |
| 6. | Enterobacter cloaca deposited with ATCC on Nov. 28, 2001 | CBTCC/ MICRO/1 | PTA-3882 | ATCC 29893 |
| 7. | Klebsiella oxytoca deposited with DSMZ on May 28, 2002 | CBTCC/ MICRO/5 | DSM 15080 | ATCC 15764 |
| 8. | Citrobacter amalonaticus deposited with DSMZ on May 28, 2002 | CBTCC/ MICRO/2 | DSM 15079 | ATCC 25406 |
| 9. | Enterobacter sakazaki deposited with DSMZ on May 28, 2002 | CBTCC/ MICRO/6 | DSM 15063 | ATCC 12868 |

The invention further provides a process for the preparation of immobilized microbial consortium and the attachment of the same with an oxygen probe useful for the estimation of BOD load of a wide variety of industrial waste-waters, which comprises:

a) isolating a range of bacterial strains from sewage collected from sewage treatment plant;

b) culturing the said strains on nutrient media to get pure cultures;

c) testing the said individual pure bacterial cultures for use as seeding material in BOD analysis using glucose-glutamic acid (GGA) as a reference standard by recording BOD values exhibited by individual strains;

d) comparing the BOD values of the said bacterial strains with that of the observed BOD values using sewage as a seeding material collected from sewage treatment plant;

e) selecting the bacterial strains which have BOD values equal to or more than the BOD values of sewage as observed in step (d);

f) formulating the microbial consortium of selected bacterial strains obtained from step (e);

g) testing the formulated microbial consortium by comparing their BOD values with those of sewage used as a seeding material;

h) immobilizing the said formulated microbial consortium by inoculating bacterial strains individually, incubating the said bacterial strains, growing the said incubated strains and mixing them in equal proportions on the basis of optical density values;

i) centrifuging the resultant suspension to obtain pellets, washing the collected pellet by dissolving in $PO_4^{-3}$ buffer, 0.025–0.075 M, pH 6.4–7.2, recentrifuging the pellet;

j) collecting the pellet from step (i), dissolving in 2.0–4.0 ml $PO_4^{-3}$ buffer, 0.025–0.075 M, pH 6.4–7.2, to obtain cell slurry for cell immobilization;

k) filtering the obtained cell slurry on charged nylon membrane under vacuum for immobilization;

l) drying the immobilized microbial membrane obtained from step (k);

m) storing the dried immobilized microbial membrane obtained from step (l) preferably at 1–4° C. in $PO_4^{-3}$ buffer, 0.025–0.075 M, pH 6.4–7.2;

n) checking the viability of microorganisms in the said immobilized microbial membrane obtained from step (m);

o) attaching the immobilized microbial membrane obtained from step (m) with dissolved oxygen probe for the preparation of electrode assembly;

p) applying an external polarization voltage of –0.65 V to the said electrode assembly obtained from step (o);

q) stabilizing the electrode assembly obtained from step (p) in $PO_4^{-3}$ buffer, 0.025–0.075 M, pH 6.4–7.2, for 30–45 minutes;

r) observing the stability of the immobilized microbial membrane using. stabilized electrode assembly obtained from step (q) by measuring the change in oxygen concentration in terms of current for BOD values covering a range of GGA concentrations;

s) characterizing the immobilized microbial membrane with respect to different variables, viz., cell density 100 $\mu l$–1000 $\mu l$, phase of cell growth 4 hours–16 hours, pH 6.4–7.2 and temperature 4° C.–37° C. in terms of response time using a range of GGA concentrations as in step (r);

t) selecting an appropriate immobilized microbial membrane from step (s) and attaching to an oxygen electrode as in step (o);

u) stabilizing the complete electrode assembly obtained form step (t) as in step (q);

v) testing the said stabilized electrode assembly by observing the change in oxygen concentration in terms of current for BOD values using a range of industrial effluents ranging from 0.05%–20.0% covering low, moderate and high biodegradable effluents. The change in current being linearly proportional to the amount of biodegradable organic matter present in the effluent.

In an embodiment of the present invention, the formulated microbial consortium is obtained by inoculating a suspension of the bacteria selected from a group consisting of *Aeromonas hydrophila, Pseudomonas aeruginosa, Yersinia enterocolitica, Serratia liquefaciens, Pseudomonas fluorescens, Enterobacter cloaca, Klebsiella oxytoca, Citrobacter amalonaticus* and *Enterobacter sakazaki.*

In another embodiment of the present invention, the individual strains of the above mentioned bacteria are inoculated separately in a nutrient broth.

In a further embodiment of the present invention, the incubation of bacterial strains is carried out by gentle agitation at approximately 75–100 rpm.

In one of the embodiment of the present invention, the growth of incubated bacterial strains is carried out at a temperature ranging between 30–37° C. for a period of 16–24 hours.

In an embodiment of the present invention, the said individual strains are mixed in equal proportions.

In a further embodiment of the present invention, the resultant microbial consortium is centrifuged at appropriate rpm preferably at 8,000–12,000 rpm for a period of approximately 20–30 minutes at a temperature ranging from 1–4° C.

In another embodiment of the present invention, the resultant pellet is washed by dissolving in an appropriate quantity of $PO_4^{-3}$ buffer, 0.025–0.075 M, pH 6.4–7.2 and recentrifuged at an approximate rpm in the range 8,000–12,000 rpm at a temperature preferably at 4° C.

In an embodiment of the present invention, the resultant cell pellet obtained is immobilized by dissolving in 1.0–2.0 ml of phosphate buffer ranging between 0.025–0.075 M, pH 6.4–7.2 to obtain cell slurry.

In one of the embodiment of the present invention, the resulting cell slurry is filtered on charged nylon membrane under vacuum.

In an embodiment of the present invention, the immobilized microbial membrane is dried at appropriate temperature, ranging between 25–35° C., for a period ranging between 4–6 hours.

In a further embodiment of the present invention, the dried immobilized membrane is stored in phosphate buffer, 0.05M, pH 6.8 at appropriate temperature ranging between 1–4° C.

In one of the embodiment of the present invention, the prepared immobilized microbial membrane is placed on nutrient agar plate and incubated at temperature ranging between 30° C.–37° C. for a period of 16–24 hours to observe the bacterial growth for viability of immobilized microorganisms.

The invention further provides a method for the estimation of BOD which comprises of an immobilized microbial membrane.

In one of the embodiment of the present invention, the dried immobilized microbial membrane is attached to dissolved oxygen probe with O ring for the preparation of electrode assembly.

In an embodiment of the present invention, the stability of the immobilized microbial membrane stored at different temperatures ranging from 4° C.–37° C. was observed using electrode assembly. The response was observed in terms of change in current.

In another embodiment of the present invention, the stable and viable immobilized microbial membrane was used for rapid and reliable BOD analysis using GGA as a reference standard in the concentration range of 30–300 mg/l.

In a further embodiment of the present invention, the immobilized microbial membrane was used for rapid and reliable BOD analysis of industrial effluents ranging from low, moderate to high biodegradable organic matter.

The invention, further described with references to the examples given below and shall not be construed, to limit the scope of the invention.

EXAMPLE I

Two loops from agar plates of *Aeromonas hydrophila, Pseudomonas aeruginosa, Yersinia enterocolitica, Serratia liquefaciens, Pseudomonas fluorescens, Enterobacter cloaca, Klebsiella oxytoca, Citrobacter amalonaticus,* and *Enterobacter sakazaki* were inoculated separately in 500 ml of nutrient broth. All the cultures were incubated at 37° C. for 16–24 hours in an incubator shaker at 75 rpm. After incubation, optical density was measured at 650 nm. Optical density of all the bacteria was maintained to 0.5 either by diluting or concentrating the bacterial suspension. All the individual bacterial suspensions were mixed thoroughly and centrifuged at 10,000 rpm for 30 minutes at 4° C. The pellet was washed by dissolving it in small volume of phosphate buffer, 0.05 M, pH 6.8 and recentrifuged at 10,000 rpm for 30 minutes at 4° C.

The pellet of microbial consortium prepared as described above was dissolved in 2.0 ml phosphate buffer, 0.05 Ml pH 6.8 to obtain cell slurry. The cell slurry was mixed with 10.0 ml of 2% polyvinyl alcohol (mw. 70,000 to 1,00,000) in luke warm distilled water. A strip of nylon net (4×4) was tightly bound to a glass plate. The prepared solution of polyvinyl alcohol with cell slurry was spread onto the tightly bound nylon net. The immobilized microbial membrane was left for drying for 4–6 hours. The dried immobilized microbial membrane was stored in 0.05 M phosphate buffer, pH6.8 at 4° C. The prepared immobilized microbial membrane was not stable due to the low retaining capacity of the membrane.

EXAMPLE II

Two loops from agar plates of *Aeromonas hydrophila, Pseudomonas aeruginosa, Yersinia enterocolitica, Serratia liquefaciens, Pseudomonas fluorescens, Enterobacter cloaca, Klebsiella oxytoca, Citrobacter amalonaticus*, and *Enterobacter sakazaki* were inoculated separately in 500 ml of nutrient broth. All the cultures were incubated at 37° C. for 16–24 hours in an incubator shaker at 75 rpm. After incubation, optical density was measured at 650 nm. Optical density of all the bacteria was maintained to 0.5 either by diluting or concentrating the bacterial suspension. All the individual bacterial suspensions were mixed thoroughly and centrifuged at 10,000 rpm for 30 minutes at 4° C. The pellet was washed by dissolving it in small volume of phosphate buffer, 0.05 M, pH 6.8 and recentrifuged at 10,000 rpm for 30 minutes at 4° C.

The pellet of microbial consortium prepared as described above was dissolved in 2.0 ml phosphate buffer, 0.05 M, pH 6.8 to obtain cell slurry. The cell slurry was filtered under vacuum on charged nylon membrane. The immobilized microbial membrane was left for drying for 4–6 hours. The dried immobilized microbial membrane was stored in 0.05 M phosphate buffer, pH6.8 at 4° C. The microbial consortium immobilized on charged nylon membrane was found to be stable, so this membrane was selected for further study.

EXAMPLE III

The selected immobilized microbial membrane was further characterized with respect to different phases of cell growth as presented in Table1(a-d). For this, two loops from agar plates of *Aeromonas hydrophila, Pseudomonas aeruginosa, Yersinia enterocolitica, Serratia liquefaciens, Pseudomonas fluorescens, Enterobacter cloaca, Klebsiella oxytoca, Citrobacter amalonaticus*, and *Enterobacter sakazaki* were. inoculated separately in 500 ml of nutrient broth. All the cultures were incubated at 37° C. for different timings ranging between 4–16 hours in an incubator shaker at 75 rpm. After incubation, optical density was measured at 650 nm. Optical density of all the bacteria grown at different phases was maintained to 0.5 either by diluting or concentrating the bacterial suspension separately. All the bacterial suspensions were mixed thoroughly and centrifuged at 10,000 rpm for 30 minutes at 4° C. The pellets of bacterial cultures grown at different phases were washed by dissolving them in small volume of phosphate buffer, 0.05 M, pH 6.8 and recentrifuged at 10,000 rpm for 30 minutes at 4° C.

The pellets of microbial consortium prepared at different phases of growth as described above were redissolved separately in 2.0 ml of phosphate buffer, 0.05 M, pH 6.8 to obtain cell slurry. The prepared cell slurry of different growth phases were filtered on charged nylon membrane separately under vacuum. The immobilized microbial membranes of different phases of cell growth were dried for 4–6 hours. The dried immobilized microbial membranes were stored in 0.05 M phosphate buffer, pH 6.8 at 4° C.. The said immobilized microbial membranes were used for the response study using GGA as a reference standard. The immobilized microbial membrane prepared using 8 hours grown microbial cells was giving better response in comparison to other immobilized microbial membranes and selected for further use.

TABLE 1a

Characterization of immobilized microbial membrane with respect to different phases of cell growth

| TIME | ΔI AFTER 4 hours OF CELL GROWTH GGA CONCENTRATION (mg/l) | | | | | | |
|---|---|---|---|---|---|---|---|
| (min) | 30 | 60 | 90 | 120 | 180 | 240 | 300 |
| 0 | 0 | 0 | 0 | 0 | 0 | 0 | 0 |
| 30 | 20 | 40 | 30 | 30 | 80 | 60 | 30 |
| 60 | 10 | 80 | 60 | 70 | 140 | 90 | 80 |
| 90 | 30 | 120 | 100 | 110 | 190 | 140 | 140 |
| 120 | 60 | 150 | 120 | 170 | 230 | 210 | 200 |
| 150 | 50 | 180 | 150 | 210 | 260 | 280 | 240 |
| 180 | 40 | 190 | 190 | 230 | 270 | 300 | 280 |
| 210 | 30 | 200 | 190 | 250 | 260 | 310 | 270 |
| 240 | 40 | 210 | 180 | 240 | 270 | 320 | 260 |
| 270 | 60 | 190 | 190 | 250 | 270 | 310 | 270 |
| 300 | 50 | 200 | 200 | 250 | 260 | 300 | 260 |

TABLE 1b

Characterization of immobilized microbial membrane with respect to different phases of cell growth

| TIME | ΔI AFTER 8 hours OF CELL GROWTH GGA CONCENTRATION (mg/l) | | | | | | |
|---|---|---|---|---|---|---|---|
| (min) | 30 | 60 | 90 | 120 | 180 | 240 | 300 |
| 0 | 0 | 0 | 0 | 0 | 0 | 0 | 0 |
| 30 | 50 | 10 | 50 | 70 | 110 | 80 | 120 |
| 60 | 100 | 90 | 90 | 90 | 200 | 140 | 240 |
| 90 | 160 | 170 | 140 | 130 | 210 | 270 | 350 |
| 120 | 210 | 180 | 240 | 150 | 300 | 340 | 410 |
| 150 | 230 | 220 | 270 | 210 | 380 | 390 | 530 |
| 180 | 220 | 260 | 300 | 260 | 370 | 450 | 620 |
| 210 | 230 | 270 | 290 | 340 | 410 | 520 | 670 |
| 240 | 250 | 260 | 310 | 360 | 390 | 530 | 660 |
| 270 | 230 | 270 | 300 | 350 | 390 | 540 | 670 |
| 300 | 250 | 260 | 290 | 360 | 400 | 530 | 660 |

TABLE 1c

Characterization of immobilized microbial membrane with respect to different phases of cell growth

| TIME | ΔI AFTER 12 hours OF CELL GROWTH GGA CONCENTRATION (mg/l) | | | | | | |
|---|---|---|---|---|---|---|---|
| (min) | 30 | 60 | 90 | 120 | 180 | 240 | 300 |
| 0 | 0 | 0 | 0 | 0 | 0 | 0 | 0 |
| 30 | 10 | 20 | 30 | 10 | 40 | 20 | 10 |
| 60 | 20 | 90 | 70 | 90 | 80 | 50 | 40 |
| 90 | 40 | 140 | 90 | 210 | 170 | 80 | 60 |
| 120 | 50 | 150 | 110 | 270 | 190 | 90 | 50 |
| 150 | 30 | 170 | 120 | 280 | 230 | 70 | 70 |
| 180 | 80 | 140 | 130 | 300 | 240 | 80 | 60 |
| 210 | 50 | 130 | 110 | 310 | 250 | 70 | 40 |
| 240 | 60 | 150 | 120 | 300 | 240 | 60 | 50 |
| 270 | 70 | 160 | 110 | 300 | 260 | 80 | 40 |
| 300 | 30 | 150 | 130 | 310 | 240 | 70 | 50 |

TABLE 1d

Characterization of immobilized microbial membrane with respect to different phases of cell growth

| TIME (min) | ΔI AFTER 16 hours OF CELL GROWTH GGA CONCENTRATION (mg/l) | | | | | | |
|---|---|---|---|---|---|---|---|
| | 30 | 60 | 90 | 120 | 180 | 240 | 300 |
| 0 | 0 | 0 | 0 | 0 | 0 | 0 | 0 |
| 30 | 20 | 30 | 50 | 30 | 10 | 30 | 10 |
| 60 | 60 | 90 | 110 | 80 | 30 | 60 | 30 |
| 90 | 50 | 140 | 190 | 150 | 30 | 50 | 40 |
| 120 | 40 | 200 | 270 | 220 | 40 | 40 | 80 |
| 150 | 30 | 280 | 260 | 230 | 30 | 70 | 50 |
| 180 | 60 | 340 | 280 | 210 | 40 | 20 | 40 |
| 210 | 30 | 350 | 270 | 220 | 30 | 30 | 30 |
| 240 | 40 | 340 | 270 | 210 | 20 | 50 | 30 |
| 270 | 10 | 350 | 280 | 230 | 40 | 40 | 40 |
| 300 | 30 | 350 | 280 | 240 | 30 | 60 | 30 |

EXAMPLE IV

Table 2(a–c) represents the characterization of the selected immobilized microbial membrane with respect to cell density. For this, two loops from agar plates of *Aeromonas hydrophila, Pseudomonas aeruginosa, Yersinia enterocolitica, Serratia liquefaciens, Pseudomonas fluorescens, Enterobacter cloaca, Klebsiella oxytoca, Citrobacter amalonaticus*, and *Enterobacter sakazaki* were inoculated separately in 500 ml of nutrient broth. All the cultures were incubated at 37° C. for 8 hours in an incubator shaker at 75 rpm. After incubation, optical density was measured at 650 nm. Optical density of all the bacteria was maintained to 0.5 either by diluting or concentrating the bacterial suspension separately. All the bacterial suspensions were mixed thoroughly and centrifuged at 10,000 rpm for 30 minutes at 4° C. The pellet of mixed bacterial cultures was washed by dissolving them in small volume of phosphate buffer, 0.05 M, pH 6.8 and recentrifuged at 10,000 rpm for 30 minutes at 4° C. The pellet of microbial consortium prepared as described above was redissolved separately in 2.0 ml of phosphate buffer, 0.05 M, pH 6–8 to obtain cell slurry.

Five different aliquots ranging from 100 μl to 1000 μl of the prepared cell slurry were filtered on charged nylon membrane separately under vacuum. The immobilized microbial membranes having different cell density were dried for 4–6 hours. All the dried immobilized microbial membranes were stored in 0.05 M phosphate buffer, pH 6.8 at 4° C. The said immobilized microbial membranes were used for the response study using GGA as a reference standard. The immobilized microbial membrane of 100 μl cell density of 8 hours grown cells was giving best response and selected for further study.

TABLE 2a

Characterization of selected immobilized microbial membrane with 100 μl cell slurry using a range of GGA concentrations

| TIME (min) | ΔI with different GGA Concentrations (mg/l) | | | | | | |
|---|---|---|---|---|---|---|---|
| | 30 | 60 | 90 | 120 | 180 | 240 | 300 |
| 0 | 0 | 0 | 0 | 0 | 0 | 0 | 0 |
| 30 | 30 | 80 | 60 | 40 | 80 | 90 | 110 |
| 60 | 40 | 100 | 100 | 150 | 210 | 220 | 230 |
| 90 | 80 | 120 | 190 | 180 | 330 | 350 | 370 |
| 120 | 90 | 160 | 240 | 250 | 420 | 510 | 450 |
| 150 | 130 | 200 | 320 | 380 | 480 | 590 | 580 |
| 180 | 200 | 240 | 360 | 320 | 470 | 570 | 670 |
| 210 | 210 | 290 | 380 | 330 | 460 | 580 | 680 |
| 240 | 200 | 290 | 390 | 330 | 470 | 550 | 680 |
| 270 | 200 | 280 | 380 | 320 | 470 | 570 | 670 |
| 300 | 200 | 290 | 380 | 330 | 470 | 570 | 670 |

TABLE 2b

Characterization of selected immobilized microbial membrane with 500 μl cell slurry using a range of GGA concentrations

| TIME (min) | ΔI with different GGA Concentrations (mg/l) | | | | | | |
|---|---|---|---|---|---|---|---|
| | 30 | 60 | 90 | 120 | 180 | 240 | 300 |
| 0 | 0 | 0 | 0 | 0 | 0 | 0 | 0 |
| 30 | 30 | 20 | 50 | 30 | 70 | 230 | 140 |
| 60 | 80 | 40 | 110 | 130 | 250 | 350 | 350 |
| 90 | 110 | 100 | 170 | 180 | 310 | 470 | 400 |
| 120 | 140 | 160 | 290 | 310 | 430 | 550 | 530 |
| 150 | 130 | 22 | 350 | 300 | 470 | 530 | 600 |
| 180 | 140 | 0200 | 360 | 360 | 500 | 560 | 620 |
| 210 | 150 | 240 | 350 | 410 | 510 | 560 | 630 |
| 240 | 140 | 250 | 340 | 450 | 520 | 550 | 630 |
| 270 | 140 | 250 | 360 | 460 | 510 | 550 | 620 |
| 300 | 140 | 260 | 360 | 450 | 510 | 550 | 630 |

TABLE 2c

Characterization of selected immobilized microbial membrane with 1000 μl cell slurry using a range of GGA concentrations

| TIME (min) | ΔI with different GGA Concentrations (mg/l) | | | | | | |
|---|---|---|---|---|---|---|---|
| | 30 | 60 | 90 | 120 | 180 | 240 | 300 |
| 0 | 0 | 0 | 0 | 0 | 0 | 0 | 0 |
| 30 | 0 | 50 | 180 | 260 | 80 | 290 | 300 |
| 60 | 10 | 80 | 110 | 410 | 260 | 470 | 490 |
| 90 | 60 | 100 | 210 | 470 | 400 | 530 | 510 |
| 120 | 140 | 220 | 270 | 550 | 480 | 600 | 580 |
| 150 | 240 | 290 | 360 | 660 | 590 | 710 | 650 |
| 180 | 190 | 310 | 440 | 730 | 620 | 780 | 800 |
| 210 | 180 | 320 | 530 | 780 | 700 | 800 | 860 |
| 240 | 190 | 330 | 530 | 800 | 710 | 850 | 870 |
| 270 | 180 | 310 | 520 | 810 | 710 | 860 | 860 |
| 300 | 190 | 320 | 530 | 800 | 710 | 860 | 860 |

EXAMPLE V

The viability study of the selected immobilized microbial membranes of 8 hours grown microbial cells having cell slurry of 100 μl stored at different temperatures ranging from 4° C.–37° C., pH 6.8, were carried out by observing the bacterial growth when the immobilized microbial membrane was placed; on the nutrient agar plate and incubated at 37° C. for the desired time period.

Table 3 represents the viability of immobilized microbial membranes stored at different temperatures.

TABLE 3

Viability study of immobilized microbial membrane stored at different temperatures

| TIME (days) | 4° C. | 15° C. | 25° C. | 37° C. |
|---|---|---|---|---|
| 15 | + + + + | + + + + | + + + + | + + + |
| 30 | + + + + | + + + | + + + | + + |
| 45 | + + + + | + + + | + + | + |
| 60 | + + + + | + + + | + + | + |
| 75 | + + + + | + + | + | + |
| 90 | + + + | + | + | − |
| 120 | + + + | + | + | − |
| 150 | + + + | + | − | − |
| 180 | + + + | + | − | − |

+ + + + excellent growth
+ + + very good growth
+ + good growth
+ fair growth
− poor growth On storage, it was observed that the immobilized microbial membrane stored at a temperature of 4° C. was viable for the longest time period.

EXAMPLE VI

The viability study of the selected immobilized microbial membranes having cell slurry of 100 $\mu l$ of 8 hours grown microbial cells, stored at different pH ranging from 6.4–7.2 and temperature 4° C. was carried out by observing the bacterial growth when the immobilized microbial: membrane was placed on the nutrient agar plate and incubated at 37° C. for the desired time period.

Table 4 represents the viability of microbial consortium immobilized on charged nylon membrane stored at different pH.

TABLE 4

Viability study of immobilized microbial membrane stored at different pH

| TIME (days) | 6.4 | 6.6 | 6.8 | 7.0 | 7.2 |
|---|---|---|---|---|---|
| 15 | + + + | + + + | + + + + | + + + + | + + + + |
| 30 | + + | + + + | + + + + | + + + + | + + + |
| 45 | + + | + + + | + + + + | + + + + | + + + |
| 60 | + | + + + | + + + + | + + + + | + + + |
| 75 | + | + + | + + + + | + + + | + + |
| 90 | − | + + | + + + | + + + | + + |
| 120 | − | + | + + + | + + + | + |
| 150 | − | + | + + + | + + | + |
| 180 | − | + | + + + | + + | − |

+ + + + Excellent growth
+ + + Very good growth
+ + Good growth
+ Fair growth
− Poor growth On storage, it was observed that the immobilized microbial membrane stored in buffer of pH 6.8 was viable for the longest time interval.

EXAMPLE VII

The electrode assembly was prepared by attaching the selected immobilized microbial membrane to dissolved oxygen probe. An external source of −0.65 V is applied to the system to get the actual reduction of oxygen at cathode. This prepared electrode assembly was used for checking the stability of immobilized microbial membrane.

EXAMPLE VIII

Table 5 represents the stability study of the selected microbial membrane immobilized on charged nylon membrane by storing at different temperatures for 180 days. For this, the immobilized microbial membrane of 8 hours grown microbial cells having 100 $\mu l$ cell slurry, stored at a temperature ranging from 4° C.–37° C., pH 6.8 attached with dissolved oxygen probe for the response study using the prepared electrode assembly.

TABLE 5

Stability study of immobilized microbial membrane stored at different temperatures

| TIME (days) | 4° C. | 15° C. | 25° C. | 37° C. |
|---|---|---|---|---|
| 15 | + + + + | + + + + | + + + | + + |
| 30 | + + + + | + + + | + + | + + |
| 45 | + + + + | + + | + | + |
| 60 | + + + + | + + | + | − |
| 75 | + + + | + | − | − |
| 90 | + + + | − | − | − |
| 120 | + + + | − | − | − |
| 150 | + + | − | − | − |
| 180 | + + | − | − | − |

+ + + + Excellent growth
+ + + Very good growth
+ + Good growth
+ Fair growth
− Poor growth On storage, it was observed that the immobilized microbial membrane gave best response when stored at 4° C.

EXAMPLE IX

The stability studies of the selected immobilized microbial membrane of 8 hours grown microbial cells having 100 $\mu l$ cell slurry were carried out by storing in different pH ranging from 6.4–7.2.

Table 6 represents the change in oxygen concentration in terms of current by immobilized microbial membranes when stored at different pH values.

TABLE 6

Stability study of immobilized microbial membrane stored at different pH

| TIME (days) | 6.4 | 6.6 | 6.8 | 7.0 | 7.2 |
|---|---|---|---|---|---|
| 15 | + + + | + + + | + + + + | + + + + | + + + |
| 30 | + + | + + + | + + + + | + + + + | + + |
| 45 | + | + + | + + + + | + + + | + + |
| 60 | + | + + | + + + + | + + + | + |
| 75 | − | + | + + + + | + + | + |
| 90 | − | + | + + + | + + | + |
| 120 | − | − | + + + | + | + |
| 150 | − | − | + + + | + | − |
| 180 | − | − | + + | + | − |

+ + + + Excellent growth
+ + + Very good growth
+ + Good growth
+ Fair growth
− Poor growth On storage, it was observed that the immobilized microbial membrane stored in pH 6.8 gave best response.

EXAMPLE X

The prepared electrode assembly was used to observe the change in oxygen concentration in terms of current using GGA, as a reference standard in BOD analysis.

Table 7 represents change in current of GGA concentration ranging between 30–300 mg/l at regular time intervals Table 7 depicts the change in oxygen concentration in terms of current with increasing GGA concentration. It is observed that higher is the GGA concentration, more is the change in current. This is indicative of the fact that at higher GGA concentration, there is more organic matter, thereby utilizing more oxygen for its oxidation. The utilization of oxygen leads to a decrease in oxygen concentration around the electrode assembly, until a steady state is reached. The steady state shows that the diffusion of oxygen from outside and its utilization are in equilibrium.

TABLE 7

Change in current with GGA concentrations ranging between 30–300 mg/l at regular time intervals

| TIME (min) | GGA CONCENTRATION (mg/l) | | | | | | |
|---|---|---|---|---|---|---|---|
| | 30 ΔI | 60 ΔI | 90 ΔI | 120 ΔI | 180 ΔI | 240 ΔI | 300 ΔI |
| 0 | 0 | 0 | 0 | 0 | 0 | 0 | 0 |
| 30 | 30 | 10 | 50 | 80 | 60 | 40 | 120 |
| 60 | 110 | 90 | 90 | 100 | 200 | 190 | 240 |
| 90 | 170 | 170 | 150 | 120 | 220 | 290 | 370 |
| 120 | 200 | 190 | 210 | 160 | 300 | 370 | 430 |
| 150 | 230 | 210 | 240 | 200 | 390 | 420 | 580 |
| 180 | 220 | 260 | 270 | 240 | 380 | 450 | 590 |
| 210 | 240 | 270 | 300 | 330 | 390 | 510 | 600 |
| 240 | 230 | 280 | 290 | 350 | 380 | 520 | 590 |
| 270 | 220 | 270 | 300 | 350 | 390 | 500 | 580 |
| 300 | 230 | 280 | 300 | 340 | 390 | 510 | 590 |

EXAMPLE XI

The prepared immobilized microbial membrane of 8 hours grown microbial cells having 100 μl cell slurry stored in 0.05 M phosphate buffer, pH 6.8 at a temperature of 4° C. attached to the electrode; assembly was used to observe the change in oxygen concentration in terms of current of various industrial effluents covering a range from 0.5–20.0% of low, moderate and high biodegradable effluents.

Table 8 represents the change in oxygen concentration in terms of current for rapid and reliable BOD estimation by immobilized microbial membrane of various industrial effluents.

The results indicate that the change in current is linearly proportional to the amount of biodegradabkle organic matter present in the sample.

TABLE 8a

CHANGE IN CURRENT (ΔI) OF INDUSTRIAL SAMPLE WITH HIGH BIODEGRADABLE ORGANIC LOAD

| TIME (min) | % OF SAMPLE | | | | | | | | |
|---|---|---|---|---|---|---|---|---|---|
| | 0.5 | 1.0 | 2.0 | 4.0 | 6.0 | 8.0 | 10.0 | 15.0 | 20.0 |
| 0 | 0 | 0 | 0 | 0 | 0 | 0 | 0 | 0 | 0 |
| 30 | 30 | 40 | 50 | 60 | 210 | 140 | 160 | 170 | 140 |
| 60 | 70 | 90 | 110 | 90 | 410 | 340 | 370 | 330 | 240 |
| 90 | 150 | 100 | 150 | 160 | 530 | 510 | 530 | 510 | 360 |
| 120 | 140 | 150 | 170 | 320 | 740 | 630 | 670 | 670 | 470 |
| 150 | 200 | 180 | 210 | 410 | 780 | 700 | 760 | 710 | 610 |
| 180 | 280 | 270 | 240 | 520 | 800 | 740 | 780 | 720 | 600 |
| 210 | 380 | 340 | 290 | 570 | 800 | 780 | 770 | 710 | 590 |
| 240 | 530 | 380 | 340 | 540 | 790 | 770 | 780 | 700 | 600 |
| 270 | 550 | 410 | 420 | 540 | 800 | 770 | 770 | 710 | 600 |
| 300 | 570 | 500 | 470 | 540 | 800 | 780 | 770 | 710 | 610 |

TABLE 8b

CHANGE IN CURRENT (ΔI) OF INDUSTRIAL SAMPLE WITH MODERATE BIODEGRADABLE ORGANIC LOAD

| TIME (min) | % OF SAMPLE | | | | | | | | |
|---|---|---|---|---|---|---|---|---|---|
| | 0.5 | 1.0 | 2.0 | 4.0 | 6.0 | 8.0 | 10.0 | 15.0 | 20.0 |
| 0 | 0 | 0 | 0 | 0 | 0 | 0 | 0 | 0 | 0 |
| 30 | 30 | 20 | 70 | 110 | 120 | 80 | 40 | 80 | 90 |
| 60 | 50 | 40 | 80 | 130 | 140 | 120 | 90 | 140 | 240 |
| 90 | 160 | 50 | 90 | 170 | 190 | 190 | 140 | 190 | 320 |
| 120 | 220 | 30 | 100 | 210 | 240 | 230 | 220 | 310 | 450 |
| 150 | 220 | 40 | 120 | 270 | 300 | 250 | 270 | 410 | 560 |
| 180 | 220 | 50 | 130 | 260 | 350 | 320 | 360 | 450 | 640 |
| 210 | 200 | 60 | 170 | 250 | 380 | 390 | 450 | 520 | 730 |
| 240 | 220 | 60 | 160 | 270 | 400 | 440 | 500 | 570 | 840 |
| 270 | 210 | 70 | 180 | 260 | 410 | 500 | 590 | 650 | 850 |
| 300 | 220 | 60 | 200 | 270 | 420 | 510 | 660 | 730 | 850 |

TABLE 8c

CHANGE IN CURRENT (ΔI) OF INDUSTRIAL SAMPLE WITH LOW BIODEGRADABLE ORGANIC LOAD

| TIME (min) | % OF SAMPLE | | | | | | | | |
|---|---|---|---|---|---|---|---|---|---|
| | 0.5 | 1.0 | 2.0 | 4.0 | 6.0 | 8.0 | 10.0 | 15.0 | 20.0 |
| 0 | 0 | 0 | 0 | 0 | 0 | 0 | 0 | 0 | 0 |
| 30 | 0 | 10 | 40 | 30 | 10 | 0 | 0 | 0 | 0 |
| 60 | 20 | 30 | 60 | 50 | 50 | 20 | 10 | 0 | 0 |
| 90 | 40 | 60 | 70 | 80 | 20 | 30 | 20 | 10 | 0 |
| 120 | 40 | 80 | 100 | 70 | 30 | 40 | 50 | 0 | 10 |
| 150 | 70 | 80 | 90 | 60 | 50 | 50 | 60 | 20 | 0 |
| 180 | 90 | 130 | 90 | 50 | 80 | 50 | 40 | 10 | 10 |
| 210 | 90 | 120 | 100 | 70 | 60 | 40 | 50 | 0 | 0 |
| 240 | 110 | 140 | 100 | 60 | 70 | 50 | 30 | 10 | 10 |
| 270 | 120 | 130 | 100 | 90 | 50 | 50 | 40 | 20 | 20 |
| 300 | 40 | 140 | 90 | 80 | 60 | 40 | 50 | 10 | 0 |

Advantages

1. The prepared microbial consortium, acting in a synergistic way is capable of biodegrading almost all kinds of organic matter present in a wide range of industrial effluents, thereby giving rapid and reproducible BOD values.
2. The prepared immobilized charged nylon membrane is more stable as compared to the existing immobilized microbial membranes.
3. The support used for the immobilization is charged nylon membrane which being positively charged binds specifically to the negatively charged bacterial cell by adsorption as well as entrapment.
4. The support used for immobilization is non-toxic to the micro-organisms.

5. The support i.e., charged nylon membrane used for the immobilization of microorganisms is novel for rapid and reliable BOD estimation.

We claim:

1. A process for the preparation of immobilized microbial consortium which comprises:
   a) isolating a range of bacterial strains from sewage collected a from sewage treatment plant;
   b) culturing the strains on nutrient media to get pure cultures;
   c) testing the individual pure bacterial cultures for use as seeding material in BOD analysis using glucose-glutamic acid (GGA) as a reference standard by recording BOD values exhibited by individual strains;
   d) comparing the BOD values of the bacterial strains with that of the observed BOD values using sewage as a seeding/material collected from sewage treatment plant;
   e) selecting the bacterial strains which have BOD values equal to or more than the BOD values of sewage as observed in step (d);
   f) formulating the microbial consortium of selected bacterial strains obtained from step (e);
   g) testing the formulated microbial consortium by comparing their BOD values with those of sewage used as a seeding material;
   h) immobilizing the formulated microbial consortium by inoculating bacterial strains individually, incubating the bacterial strains, growing the incubated strains and mixing them in equal proportions on the basis of optical density values to obtain a suspension;
   i) centrifuging the resultant suspension to obtain pellets, washing the collected pellet by dissolving in $PO_4^{-3}$ buffer, 0.025–0.075 M, pH 6.4–7.2, recentrifuging the pellet;
   j) collecting the pellet from step (i), dissolving in 2.0–4.0 ml $PO_4^{-3}$ buffer, 0.025–0.075 M, pH 6.4–7.2, to obtain cell slurry for cell immobilization;
   k) filtering the obtained cell slurry on charged nylon membrane under vaccum for immobilization;
   l) drying the immobilized microbial membrane obtained from step (k);
   m) storing the dried immobilized microbial membrane obtained from step (l); and
   n) checking the viability of microorganisms in the immobilized microbial membrane obtained from step (m).

2. A process as claimed in claim 1, wherein the formulated microbial consortium is obtained by inoculating a suspension of the bacteria selected from a group consisting of *Aeromonas hydrophila, Pseudomonas aeruginosa, Yersinia enterocolitica, Serratia liquefaciens, Pseudomonas fluorescens, Enterobacter cloaca, Klebsiella oxytoca, Citrobacter amalonaticus* and *Enterobacter sakazaki*.

3. A process as claimed in claim 1, wherein the strains of the bacteria used in step h) of claim 1 are inoculated separately in a nutrient broth.

4. A process as claimed in claim 1, wherein the incubation of bacterial strains is carried out by gentle agitation at approximately 75–100 rpm.

5. A process as claimed in claim 1, wherein the incubation of bacterial strains is carried out at a temperature ranging between 30° C.–37° C. for a period of 16–18 hours.

6. A process as claimed in claim 1, wherein the resultant microbial consortium is centrifuged at 8,000–12,000 rpm for a period of approximately 20–30 minutes at a temperature of 1–4° C.

7. A process as claimed in claim 1, wherein the immobilized microbial membranes are dried for 4–6 hours at a temperature ranging between 25° C.–35° C.

8. A process as claimed in claim 1, wherein the viability of the immobilized microbial membrane is checked by storing in $PO_4^{-3}$ buffer, 0.05–2.0 M, at appropriate pH and temperature ranging between 6.4–7.2 and 4° C.–37° C., respectively.

9. A process for the estimation of BOD using an immobilized microbial consortium, as claimed in claim 1, which comprises:
   a) attaching the immobilized microbial membrane, as claimed in claim 1, with dissolved oxygen probe for the preparation of electrode assembly;
   b) applying an external polarization voltage of −0.65 V to the said electrode assembly obtained from step (a);
   c) stabilizing the electrode assembly obtained from step (b) in $PO_4^{-3}$ buffer, 0.025–0.075 M, pH 6.4–7.2, for 30–45 minutes;
   d) observing the stability of the immobilized microbial membrane using stabilized electrode assembly obtained from step (c) by measuring the change in oxygen concentration in terms of current for BOD values covering a range of GGA concentrations;
   e) characterizing the immobilized microbial membrane with respect to different variables, viz., cell density 100 μl–1000 μl, phase of cell growth 4 hours–16 hours, pH 6.4–7.2 and temperature 4° C.–37° C. in terms of response time using a range of GGA concentrations as in step (d);
   f) selecting an appropriate immobilized microbial membrane from step (e) and attaching to an oxygen electrode as in step (a);
   g) stabilizing the complete electrode assembly obtained form step (f) as in step (c);
   h) testing the said stabilized electrode assembly by observing the change in oxygen concentration in terms of current for BOD values using a range of industrial effluents ranging from 0.05%–20.0% covering low, moderate and high biodegradable effluents, wherein, the change in current being linearly proportional to the amount of biodegradable organic matter present in the effluent.

10. A process as claimed in claim 9, wherein the stability of the immobilized microbial membrane is checked by storing in $PO_4^{-3}$ buffer, 0.05–2.0 M, at appropriate pH and temperature ranging between 6.4–7.2 and 4° C.–37° C., respectively.

11. A process as claimed in claim 9, wherein an appropriate immobilized microbial membrane is selected on the basis of phase of cell growth, cell density, temperature and pH by observing the response i.e, oxygen consumption in terms of change in current with a range of GGA concentrations.

12. A process as claimed in claim 9, wherein the stabilized electrode assembly is tested by observing the change in oxygen concentration in terms of current for BOD values using GGA concentration in the range of 30–300 mg/l as a reference standard in BOD analysis.

13. A process as claimed in claim 9, wherein the stabilized electrode assembly is tested by observing the change in oxygen concentration in terms of current for BOD values using a range of industrial samples.

14. The process as claimed in claim 1 wherein the dried immobilized microbial membrane is stored at 1–4° C. in $PO_4^{-3}$ buffer, 0.025–0.075 M, and pH 6.4–7.2.

* * * * *